(12) United States Patent
Vanacker et al.

(10) Patent No.: US 6,911,030 B1
(45) Date of Patent: Jun. 28, 2005

(54) FIXING ELEMENT AND ANCILLARY FOR STABILIZING VERTEBRAE

(75) Inventors: Gerard Vanacker, Saint Maur (FR); Reinhard Zeller, Boulogne (FR)

(73) Assignee: Spinevision S.A. (FR)

( * ) Notice: Subject to any disclaimer, the term of this patent is extended or adjusted under 35 U.S.C. 154(b) by 314 days.

(21) Appl. No.: 10/019,715
(22) PCT Filed: Jun. 30, 2000
(86) PCT No.: PCT/FR00/01872

§ 371 (c)(1),
(2), (4) Date: Mar. 15, 2002

(87) PCT Pub. No.: WO01/01873

PCT Pub. Date: Jan. 11, 2001

(30) Foreign Application Priority Data

Jul. 1, 1999 (FR) .......................................... 99 08498

(51) Int. Cl.[7] .............................................. A61B 17/58
(52) U.S. Cl. ........................................................ 606/61
(58) Field of Search .............................. 606/61, 72, 73

(56) References Cited

U.S. PATENT DOCUMENTS 5,562,663 A   10/1996 Wisnewski et al.
5,696,321 A * 12/1997 Igarashi et al. ............ 73/202.5
5,899,901 A *  5/1999 Middleton ................... 606/61

FOREIGN PATENT DOCUMENTS

| DE | 41 07 480 | 9/1992 |
| EP | 0 346 521 | 12/1989 |
| EP | 0 535 623 | 4/1993 |
| EP | 0 879 579 | 11/1998 |

* cited by examiner

Primary Examiner—Glenn K. Dawson
Assistant Examiner—D. Jacob Davis
(74) Attorney, Agent, or Firm—Bachman & LaPointe, P.C.

(57) ABSTRACT

The invention concerns an osteosynthesis system, comprising at least a linking element in the form of a rod, at least two fixing elements each capable of being anchored in a vertebra, and a locking screw. The invention is characterized in that the base of the head has a general horse-saddle shape, and the head has guide means for an independent closure component designed to be fixed on the head after the linking element has been positioned in the fork of the head, said closure component being generally U-shaped whereof the branches are urged to co-operate with the branches of the fork-shaped part of the head and whereof the base comprises an internal thread for co-operating with the locking screw and the guide means provided on the head is formed by an arc-shaped shoulder on the outer side surfaces of the fork-shaped part. The invention also concerns an ancillary and an element for fixing such a system.

18 Claims, 3 Drawing Sheets

FIXING ELEMENT AND ANCILLARY FOR STABILIZING VERTEBRAE

BACKGROUND OF THE INVENTION

The present invention relates to the domain of spinal osteosynthesis intended for surgery of the vertebral column, to correct malformations of the degenerative or idiopathic, neuromuscular or tumoral, or of the traumatological type.

In prior art, it is known how to use an instrumentation comprising implants to be fixed on the bone, by screwing or by hooks and linkage elements enabling the surgeon to apply constraints for straightening or stabilising the vertebral column.

As an example, the European patent EP626828 describes such a system enabling osteosynthesis on the vertebral column, together with a linkage element between this system and the tools used for assembly and/or disassembly. This prior art document describes a device for osteosynthesis on the vertebral column, in particular for stabilising the vertebrae, comprising:

at least one linkage element in the shape of a rod.
at least two fixation elements each able to be anchored in a vertebra, these means having a head of the forked shape type whose two branches define a reception space closely U-shaped for the linkage element,
a tightening screw able to be screwed in the reception space to fix the linkage element between the two branches of the fork-shaped screw head,
the head whose bottom of the reception space is shaped in the form of a concave cup corresponding with a tilting bushing element fitted between the bottom of the reception space and the linkage element, the bushing element whose bearing surface opposite the reception space bottom is of a complementary convex shape, characterised in that the tilting bushing element is provided with a hemispherical bearing surface corresponding with the bottom of the reception space. This element is provided with a cut-out open from the tightening screw side in order to receive the linkage element in the form of a rod. The tilting bushing is maintained against the bottom of the reception space in such a way that it can tilt just as well in a plane parallel to the median plane of the reception space as in a perpendicular plane.

Patent PCT WO9101691 is also known, describing a device for straightening and propping up a vertebral column, constituted of screwed implants or hooks linked by at least two rods integrated together through the intermediary of connection and linkage elements. These rods are introduced longitudinally in grooves perpendicular to the screw, provided for this purpose in the body of the implants or hooks, then blocked in the bottom of the grooves. Integralisation of the rods is obtained with a threaded cross tie. A deformation by approaching the sides of the groove, set in the body of the implants or hooks, in order to obtain blocking of the rod in the bottom of the groove, is obtained through a system of cylindrical screw and conical threaded nut.

Patent WO9514437 is also known, revealing an implant comprising a part destined for anchoring the bone and a body for fixation on a rod, comprising two lateral branches defining a channel, this implant also comprising a threaded plug adapted in order to be screwed on the internal walls of the two branches. Another patent PCT WO9410944 describes a device comprising a connection element set between a rod or other longitudinal implant, and a bone fixation screw placed in the degenerative vertebra. This connection element comprises a ring with dimensions such that the rod can pass through. The ring is provided with screws for fixing the rod and extends radially thanks to a cylindrical arm designed to be fixed to the fixation screw of the bone and tightened on the screw. The arm and the ring constitute a single part. This device allows the surgeon to avoid deforming the rod further when the latter is in the presence of non-aligned vertebral pedicles, leaving the surgeon total freedom to choose the placing of the two axes of the fixation screw of the bone and the rod.

The problem of devices of prior art is that of maintenance of the orientation decided by the surgeon at the time of the definitive fixation and of the dissociation between the positioning of the linkage element and the insertion of the bone implant. In the devices comprising a tightening screw, the tightening of this screw has a tendency to modify the relative orientation of the linkage rods and the fixation element.

Another problem is that of adjusting the setting of the screws during the realignment stage of the vertebral column by rotation of the correction rod. This correction rod crosses through numerous vertebral implants, for example 10 to 15 implants and/or vertebral screws. Generally, each of these implants comprises a blocking screw. This blocking screw must be sufficiently tightened to avoid slipping from the vertebral implant, but not too tight in order to allow rotation of the rod without excessive friction. The adjustment of the degree of screwing of each of these blocking screws is a fastidious and delicate operation.

SUMMARY OF THE INVENTION

The aim of the invention is to avoid these inconveniences by proposing a system and an implant making it possible to preserve the degree of correction decided by the surgeon during the operations of definitive fixation and tightening of blocking screws of the linkage element. The aim is also to allow rotation of the rod during its rotational manoeuvring, with minimum friction independent of the degree of tightening of the blocking screw.

Thus, the aim of the invention concerns in its most general form a device for osteosynthesis on the vertebral column, in particular for the stabilisation of vertebrae, comprising:

at least one linkage element in the form of a rod, or plate,
at least two means of fixation each able to be anchored into a vertebra, these means having a head in the shape of a fork whose two branches define a reception space closely in the form of a "U" for the linkage element,
a blocking screw capable of being screwed in the reception space to fix the linkage element positioned between the two branches of the forked shape screw head, characterised in that the bottom of the head has the general shape of a horse saddle, in that the head has a guide means for an independent closure part capable of being fixed on the head after positioning the linkage element in the fork of the head, said closure part being in the general form of a "U" with branches coming into co-operation with the branches of the part in the shape of a "Y" fork for the head, and whose bottom comprises a threading for co-operation with the blocking screw and in that the guide means provided on the head are formed by an arched shoulder on the external lateral surfaces of the fork shaped part.

The horse-saddle shape can be described as an inverse hyperbolic paraboloid, according to a particular embodiment but it is not limited to a shape engendered by a second degree equation corresponding to a hyperbolic paraboloid.

This embodiment makes it possible first of all to insert the fixation, means on the vertebral column, then the linkage elements possibly at the same time as the closure part, then to adjust the correction independently from the locking element, and when the optimum correction has been obtained, to block each implant by the blocking screws. The tightening of the blocking screws does not modify the orientation of the fixation means because of the degree of freedom of movement of the closure part relative to the body of the fixation means.

The closure part has two lateral branches which are flexibly malleable, with an arched shoulder on the interior surfaces. The dimensions and shapes of branches and shoulders are determined in such a way as to allow the setting of the closure part by flexible spacing of the branches and the interlocking of the shoulders. The final locking of the closure part and the implant is produced by tightening the blocking screw. The guide means of the closure part on the head is formed by a complementary arched shoulder provided on the external lateral surfaces of the fork-shaped part. This arched shoulder allows rotation of the closure part relative to the head of the implant.

A variant consists of producing a closure part having a shape memory. Such a part has spread arms at rest, to allow setting on the fork-shaped part. When it is in position on the head of the hook, a modification of temperature makes the arms fold back into an anchoring position on the fork.

According to a preferred embodiment, the shoulders have contact surfaces converging closely towards the threading intended to receive the blocking screw.

According to a variant, the position of the closure part is fixed relative to the head fork. The shoulder or the interlocking means, according to this variant, do not allow a degree of rotational freedom of the closure part.

The angle of convergence is not very critical. It is only important that the contact surfaces should be oriented towards the bottom of the closure part. However, an angle of about ten degrees relative to the transversal plane would already make it possible to obtain a satisfactory guiding.

According to an embodiment variant, the head is prolonged by a lower part in the shape of a hook for maintaining the vertebral column for the setting on a pedicle, vertebra lamina or transverse process, said hook comprising a flexible lamina for temporary maintenance of the fixation.

The invention surely relates to the system comprising the components as a whole (correction rod, implants, closure parts, blocking screws). Nonetheless it also relates to the fixation element capable of being anchored onto a vertebra, for the osteosynthesis instrumentation. This fixation element can be used with linkage elements other than rods, for example a linkage element with a trapezoid or variable cross-section, or laminae, in particular laminae having linkage zones of circular cross-section.

The invention also concerns an ancillary for the implementation of a system for osteosynthesis according to the invention characterised in that it presents two jaws which come to lodge in the cut-outs provided on the head of the implant, and a device exerting a force on the rod to ensure its lateral and/or vertical displacement, with the intention of enabling the positioning of the rod in the fork. This effort can be exerted on the rod through the intermediary of the closure part with which the ancillary co-operates during the phase of setting the rod in place in the fork of the implant. The co-operation can be carried out by temporary screwing of the ancillary in the threading of the closure part.

BRIEF DESCRIPTION OF THE DRAWINGS

The invention will be better understood by reading the following description of the attached drawings wherein.

DETAILED DESCRIPTION OF THE PREFERRED EMBODIMENT(S)

Figure 1:
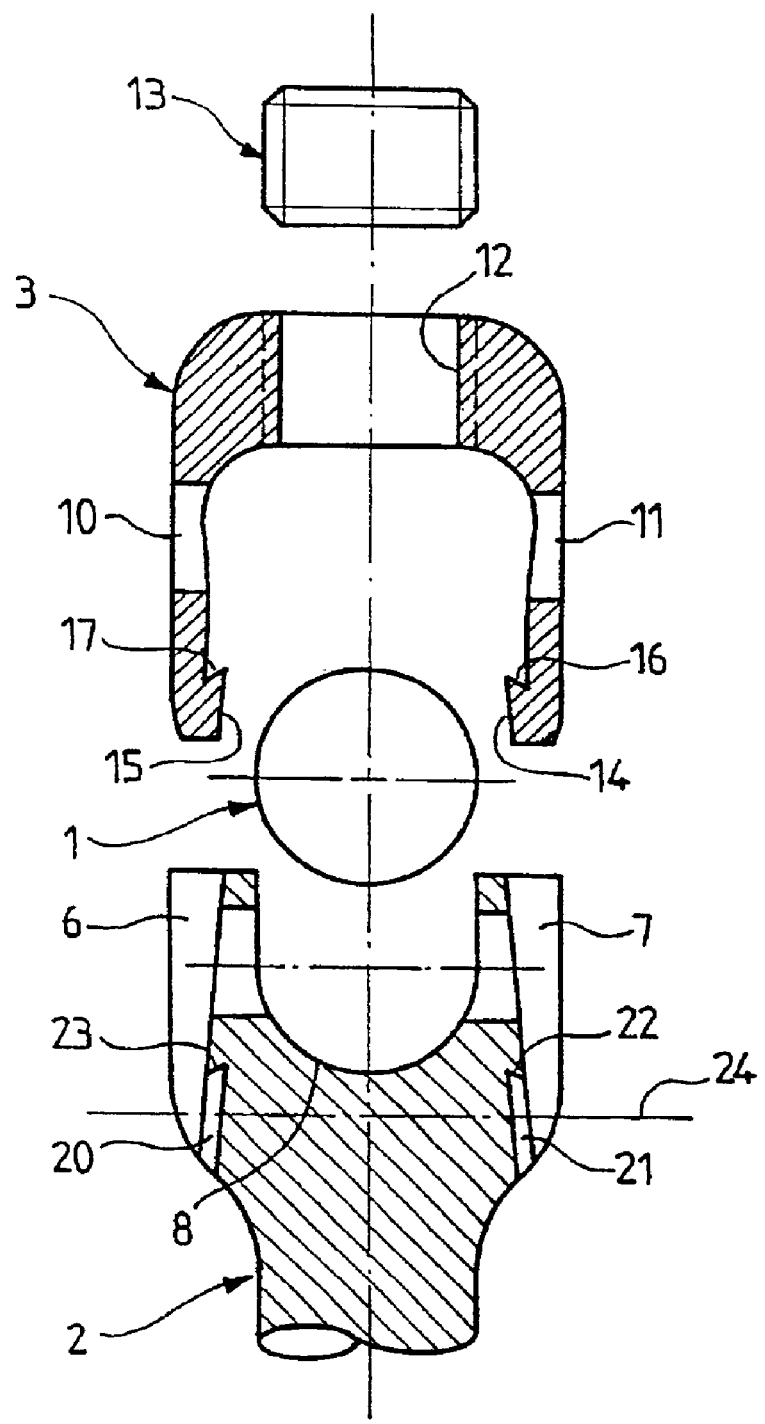
FIG. 1 shows a longitudinal cross-section of an embodiment of an osteosynthesis system according to the invention.

The osteosynthesis system according to the present invention comprises a linkage element (1), an implant (2) with a complementary closure part (3), and a blocking screw (13).

The rod (1) will not be described in greater detail since it belongs to the present state of the art and can take diverse forms. In the example given, it is formed of a metallic rod with a circular cross-section.

The implant has a fork shaped head (5), with two lateral arms (6, 7) defining a space intended to receive the linkage element (1).

The bottom (8) of the fork is generally horse-shoe shaped, with a concave curve in the transversal plane corresponding to the plane of FIG. 1, and a convex curve in the complementary plane.

The radius of the concave curve corresponds closely to the external radius of the guiding element (1). The latter thus comes into contact following a semi-peripheral line. This contact according to a line and not according to an annular surface allows a degree of pivoting freedom, and at the same time ensures more efficient blocking after tightening than in the case of a simple pinpoint contact.

The closure part (3) has a general "U" shape, with two arms (10, 11) and a bottom with a threading (12) to receive a blocking screw.

The arms (10, 11) have a spacing allowing the head to be put into place. At their lower extremity the arms (10, 11) have arched shoulders (14, 15) with an upper inclined surface (16, 17).

These arched shoulders (14, 15) co-operate with the complementary guide means (20, 21) provided on the head (5). These guide means also have an inclined arched contact surface (22, 23), and co-operate with the complementary contact surfaces (14, 15) when the closure part is set in place on the head (5). They then ensure a guiding allowing pivoting of the closure part along a transversal axis (24) and ensure the locking of the closure part (3) on the head (5), and thus the blocking of the rod (1) after tightening the screw (13).

Figure 2:
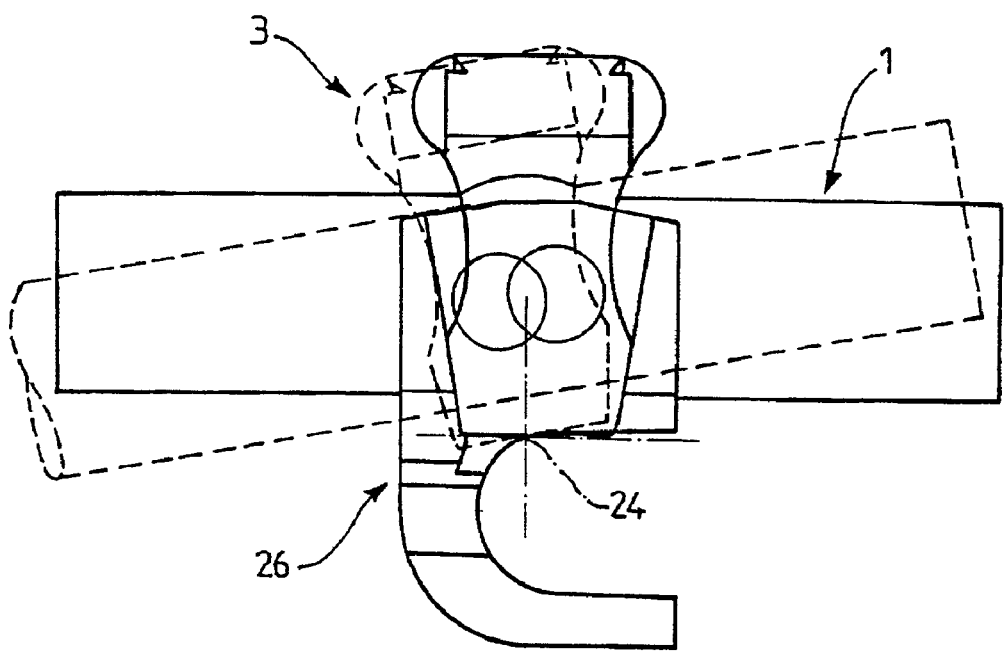
FIG. 2 shows a diagram from the side of the system according to the invention.

FIG. 2 is a side view showing that the rod (1) has a degree of freedom tilting around a transversal axis (24). This makes it possible to give the implant independence, and to position the implant by means of the hook (26) on the pedicle, and independently to search for the best orientation of the rod (1) without interference between these two restrictions. The horse-shoe shape and the mobility of the closure part make it possible to adapt the locking and to avoid de-rotation or displacement of the rod during tightening of the screw (13).

The hook (26) defines a "U-shaped" space (27) for linkage with the lamina of a vertebra. In order to ensure temporary maintenance, a flexible lamina (28) is set inside this "U" space and ensures a temporary maintenance on the bone in such a way that there is no risk of the lamina of the hook disturbing the spinal cord or any other structure. The flexible lamina (28) pushes back the hook in a posterior direction relative to the patient, and avoids lesions of the noble tissues during the phase of correction by rotation of the rod.

Figure 3:
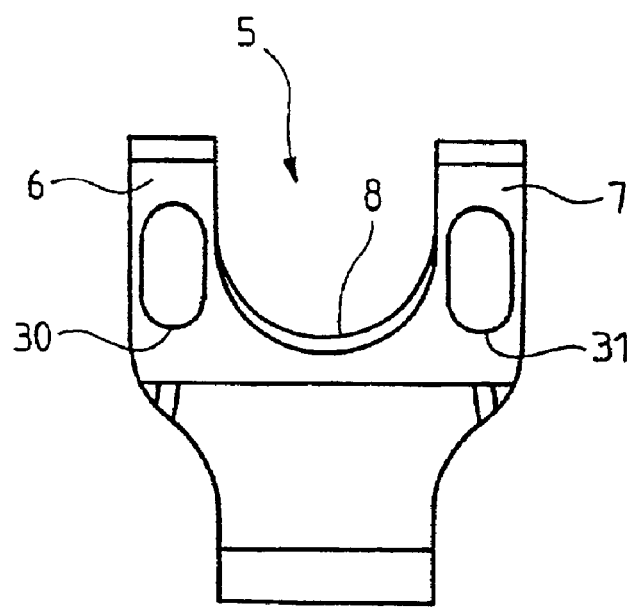
FIGS. 3 and 4 show a view of the implant according to two perpendicular faces.
Figure 4:
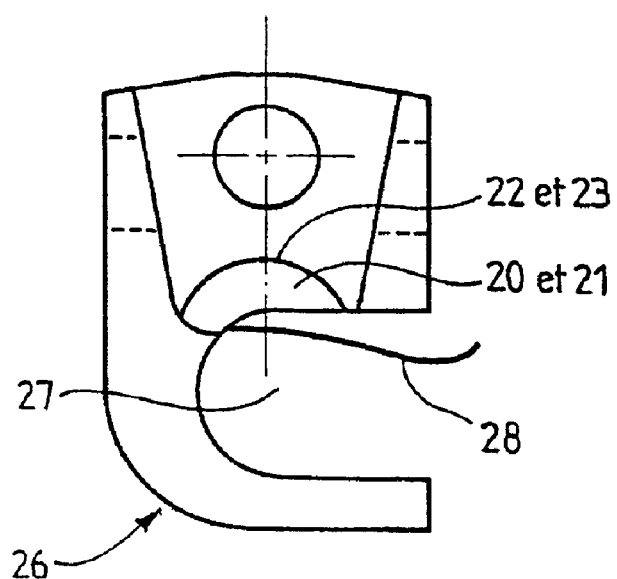

FIGS. 3 and 4 show side views of the implant, without the closure part.

The implant has two cut-outs (30, 31) allowing the passage of an instrument with two jaws to lodge in the cut-outs (30, 31), and a device exerting an effort on the rod to ensure its lateral and/or vertical displacement, in order to allow the positioning of the rod in the fork through the intermediary of the closure part (3). In this case, one part of the instrument is integrated temporarily with the closure part with the aid of a screw introduced in the threading (12) of the closure part (3).

The invention is described above as a non-limiting example. It is understood that those skilled in the art can produce diverse variants, in particular by replacing the hook by a pedicle screw, or a vertebral screw for inserting on the anterolateral face of the vertebral column.

What is claimed is:

1. A system for osteosynthesis on the vertebral column for stabilization of vertebrae comprising:
   at least one rod-shaped linkage element;
   at least two fixation means to be anchored into a vertebra;
   each said fixation means having a head in the shape of a fork having two branches, said two branches defining a reception space closely in the form of a U for receiving the at least one rod-shaped linkage element;
   said head having a bottom in the shape of a horse saddle;
   a blocking screw to be screwed in the reception space to fix the at least one linkage element between the two branches of the fork shaped head;
   an independent closure to be fixed on the head after positioning the at least one linkage element in the fork of the head;
   said independent closure part being in the general shape of a U with branches cooperating with the branches of the fork shaped part of the head;
   said closure part having a bottom which comprises a threading for cooperation with the blocking screw; and
   guide means for positioning said closure part on said head, said guide means including inclined undercut portions in external lateral surfaces of the forked shaped part of the head forming arched shoulders.

2. A system for osteosynthesis according to claim 1, further comprising said closure part having complementary shoulders and said closure part being anchored by contacting transverse surfaces of the shoulders during tightening of the blocking screw.

3. A system for osteosynthesis according to claim 2, wherein the shoulders provided on the lateral surfaces of the fork shaped head part are in the shape of an arc of a circle.

4. A system for osteosynthesis according to claim 2, wherein the closure part shoulders have inclined contact surfaces converging towards the threading for receiving the blocking screw.

5. A system according to claim 1, further comprising said head having a longitudinal axis and said independent closure being movable relative to said head about an axis transverse to said longitudinal axis.

6. A system according to claim 1, wherein said independent closure part branches comprise arms formed from a flexible material and wherein said arms are flexed to set the closure part on the head.

7. A system according to claim 1, wherein said independent closure part branches comprise arms formed from a shape memory material and wherein said closure part is set on the head by subjecting the arms to a temperature which causes the arms to fold back into an anchoring position.

8. A system according to claim 1, wherein the head has a plurality of cut-outs for allowing passage of an instrument.

9. A system according to claim 1, wherein the shoulders on said head are formed by an arc.

10. A system for osteosynthesis on the vertebral column for stabilization of vertebrae comprising:
    at least one rod-shaped linkage element;
    at least two fixation means to be anchored into a vertebra;
    each said fixation means having a head in the shape of a fork having two branches, said two branches defining a reception space closely in the form of a U for receiving the at least one rod-shaped linkage element;
    said head having a bottom in the shape of a horse saddle;
    a blocking screw to be screwed in the reception space to fix the at least one linkage element between the two branches of the fork shaped screw head;
    an independent closure part;
    said head having a guide means for said independent closure part to be fixed on the head after positioning the at least one linkage element in the fork of the head;
    said independent closure part being in the general shape of a U with branches cooperating with the branches of the fork shaped part of the head;
    said closure part having a bottom which comprises a threading for cooperation with the blocking screw;
    said guide means provided on the head being formed by an arched shoulder on external lateral surfaces of the fork shaped part of the head;
    said head being prolonged by a lower part in the shape of a hook for setting in place a pedicle; and
    said hook comprising a flexible lamina for temporary maintenance.

11. A fixing element to be anchored onto a vertebra for osteosynthesis instrumentation, said fixing element comprising:
    a head in the shape of a fork having two branches, said two branches defining a reception space closely in the form of a U for receiving a linkage element;
    said head having a bottom in the general shape of a horse saddle;
    an independent closure part;
    said head further having guide means for said independent closure part capable of being fixed on the head after said linkage element has been positioned in the fork of the head;
    said closure part being in the general form of a U with branches co-operating with the fork branches;
    said closure part having a bottom which comprises a threading for co-operation with a blocking screw; and
    said guide means being formed by inclined undercuts in external lateral surfaces of the fork shaped part of the head, said undercuts forming a pair of arched shoulders.

12. A fixing element according to claim 11, wherein the closure has a complementary shoulders and is anchored by contacting transverse surfaces of the shoulders during tightening of the blocking screw.

13. A fixing element according to claim 12, wherein the shoulders provided on lateral surfaces of the fork shaped part of the head are in the form of an arc of a circle, allowing a degree of freedom for the linkage element relative to a fixation implant on a vertebral column.

14. A fixing element according to claim 12, wherein the closure part shoulders have inclined contact surfaces converging on the threading.

15. A fixing element according to claim 11, wherein said independent closure part branches comprise arms formed from a flexible material and wherein said arms are flexed to set the closure part on the head.

16. A fixing element according to claim 11, wherein said independent closure part branches comprise arms formed from a shape memory material and wherein said closure part is set on the head by subjecting the arms to a temperature which causes the arms to fold back into an anchoring position.

17. A fixing element according to claim 11, wherein the head has a plurality of cut-outs for allowing passage of an instrument.

18. A fixing element to be anchored onto a vertebra for osteosynthesis instrumentation, said fixing element comprising:

a head in the shape of a fork having two branches, said two branches defining a reception space closely in the form of a U for receiving a linkage element;

said head having a bottom in the shape of a horse saddle;

said head further having guide means for an independent closure part capable of being fixed on the head after said linkage element has been positioned in the fork of the head;

said closure part being in the general shape of a U with branches cooperating with the fork branches;

said closure part having a bottom which comprises a threading for cooperation with a blocking screw;

said guide means being formed by an arched shoulder on external lateral surfaces of the fork shaped part of the head;

a lower part in the form of a hook for setting in place on the vertebra; and said hook comprising a flexible lamina for temporary fixation maintenance.

* * * * *